(12) United States Patent
Lüthi

(10) Patent No.: US 7,049,829 B2
(45) Date of Patent: May 23, 2006

(54) MOISTURE SENSOR WITH CAPACITIVE MOISTURE MEASURING ELEMENT AND METHOD OF DETERMINING AIR HUMIDITY

(75) Inventor: Yves Lüthi, Baar (CH)

(73) Assignee: Siemens Building Technology AG, Zurich (CH)

( * ) Notice: Subject to any disclaimer, the term of this patent is extended or adjusted under 35 U.S.C. 154(b) by 27 days.

(21) Appl. No.: 10/685,077

(22) Filed: Oct. 14, 2003

(65) Prior Publication Data

US 2004/0075445 A1 Apr. 22, 2004

(30) Foreign Application Priority Data

Oct. 18, 2002 (EP) .................................. 02023364

(51) Int. Cl.
*G01R 27/26* (2006.01)

(52) U.S. Cl. .................................. 324/664; 073/335.04

(58) Field of Classification Search ............... 73/29.01, 73/335.05, 335.04; 324/658, 694, 664, 689
See application file for complete search history.

(56) References Cited

U.S. PATENT DOCUMENTS

| | | | | |
|---|---|---|---|---|
| 4,945,863 A | | 8/1990 | Schmitz et al. ............. 123/1 A |
| 5,027,077 A | * | 6/1991 | Yanagisawa et al. ....... 324/712 |
| 5,485,747 A | * | 1/1996 | Antikainen et al. ...... 73/335.03 |
| 5,792,938 A | * | 8/1998 | Gokhfeld .................... 73/29.02 |
| 5,844,138 A | | 12/1998 | Cota .......................... 73/29.01 |
| 5,922,939 A | * | 7/1999 | Cota .......................... 73/29.01 |
| 6,073,480 A | * | 6/2000 | Gokhfeld .................... 73/29.02 |
| 6,450,026 B1 | * | 9/2002 | Desarnaud ................ 73/335.04 |
| 6,724,612 B1 | * | 4/2004 | Davis et al. ................. 361/328 |
| 6,882,165 B1 | * | 4/2005 | Ogura ......................... 324/663 |

FOREIGN PATENT DOCUMENTS

| | | |
|---|---|---|
| EP | 0 377 782 A2 | 7/1989 |
| GB | 2 284 676 | 6/1995 |

OTHER PUBLICATIONS

Lee et al, MEMS-based Humidity Sensors with Integrated Temperature Sensors for Signal Drift Compensation Sensors, 2003, Proceedings of IEEE, vol. 1, Oct. 22-24, 2003, pp. 384-388 vol. 1.*

(Continued)

*Primary Examiner*—Anjan Deb
*Assistant Examiner*—Walter Benson
(74) *Attorney, Agent, or Firm*—Maginot, Moore & Beck

(57) ABSTRACT

In a method of determining air humidity, a corrected moisture signal is calculated for a moisture signal (Hi) ascertained from electrical properties of a capacitive moisture measuring element. In a measuring phase (30) with rising relative air humidity (RH), the corrected moisture signal is the current moisture signal (Hi) increased by a correction value, whereas in a measuring phase (31) with falling relative air humidity (RH) the corrected moisture signal is the current moisture signal (Hi) reduced by a correction value. Depending on the respective properties of the moisture measuring element and the required degree of measuring accuracy, the correction value is constant or is taken into consideration in dependence on the relative air humidity RH. This method provides a higher level of measuring accuracy with a moisture sensor equipped with the moisture measuring element.

18 Claims, 3 Drawing Sheets

OTHER PUBLICATIONS

Chen, Zhi, Mao-Chang Jin and Chao Zhen, "Humidity Sensors With Reactively Evaporated $Al_2O_3$ Films as Porous Dielelectrics," Sensors and Actuators B Chemical, Aug. 1990, (5 pages).

Li, G. Q., P. T. Lai, M. Q. Huang, S. H. Zeng, B. Li and Y. C. Cheng, "A Humidity-Sensing Model for Metal-Insulator-Semiconductor Capacitors with Porous Ceramic Film," Journal of Applied Physics, Jun. 15, 2000, (5 pages).

Denton, Denice D., Maha A. S. Jaafar, Andrew R. K. Ralston, Choon Ngiap Ho, and I Li Sen-gang, "The Long Term Reliability of a Switched-Capacitor Relative Humidity Sensor System," University of Wisconsin-Madison, (4 pages).

Dokmeci, Mehmet and Khalil Najafi, "A High-Sensitivity Polyimide Capacitive Relative Humidity Sensor for Monitoring Anodically Bonded Hermetic Micropackages," Journal of Microelectromechanical Systems, vol. 10, No. 2, Jun. 2, 2001, (8 pages).

Visscher, G. J. W. and J. G. Kornet, "Long-Term Tests of Capacitive Humidity Sensors," Measurement Science & Technology, Oct. 1994, (9 pages).

Anchisini R., G. Faglia, M. C. Gallazzi, G. Sberveglieri, and G. Zerbi, "Polyphosphazene Membrane as a Very Sensitive Resistive and Capacitive Humidity Sensor," Sensors and Actuators B Chemical, 1996 (4 pages).

* cited by examiner

MOISTURE SENSOR WITH CAPACITIVE MOISTURE MEASURING ELEMENT AND METHOD OF DETERMINING AIR HUMIDITY

BACKGROUND OF THE INVENTION

1. Field of the Invention

The invention relates to a method of determining moisture with a capacitive moisture-sensitive element, and an apparatus for carrying out the method.

2. Description of Prior Art

Such apparatuses and methods are advantageously used in the heating, ventilation and air-conditioning art (HVAC) for buildings for determining the air humidity in a room or in a device for supplying or discharging air.

Capacitive moisture measuring elements deliver a capacitance value in dependence on the air humidity in the area around the measuring element. That capacitance value can be measured by means of an electronic evaluation system. A current moisture value is ascertained with the measured capacitance value, using further parameters such as temperature and comparative parameters.

Capacitive moisture measuring elements are available on the market in various different forms, and by way of example reference will be made here to 'HS11100' from Humirel, 'MiniCap2' from Panametrics, 'H5000' from Gefran, 'Hygromer C-94' from Rotronic and 'HC1000' from E+E Elektronik. The manufacturers of moisture measuring elements generally also propose circuits, by means of which air humidity can be measured. In many cases an oscillator circuit with a generally known multivibrator '555' is proposed for use of the specified moisture measuring elements. U.S. Pat. No. 5,844,138 also discloses a device of that kind in which a capacitive moisture sensor is part of an oscillator. The frequency of the oscillator is dependent on the condition of the moisture sensor and thus the moisture level.

In known devices for measuring air humidity, the capacitive moisture sensor used is considered as an ideal capacitor involving a variable capacitance. Experience has shown that this simplification, for certain uses, gives rise to unacceptably large deviations between an air humidity value ascertained in the known manner and the air humidity value which is actually present. In particular mention should be made of the fact that the properties of individual examples in the case of capacitive moisture measuring elements of the same kind can suffer from relatively severe scatter.

BRIEF SUMMARY OF THE INVENTION

The object of the present invention is to improve known methods of determining air humidity in such a way that it is possible to achieve a substantial improvement in the level of measuring accuracy with a conventional capacitive moisture measuring element. In this respect the invention also seeks to provide an apparatus with which the method can be carried into effect.

In accordance with a first aspect of the present invention, there is provided a method of determining air humidity with a capacitive moisture measuring element, comprising:

a method step in which a current moisture signal is ascertained from electrical properties of the moisture measuring element, and a method step in which a corrected moisture signal is calculated from the current moisture signal, wherein in a measuring phase with rising relative air humidity RH the corrected moisture signal is the current moisture signal increased by a correction value a(RH) and wherein in a measuring phase with falling relative air humidity RH the corrected moisture signal is the current moisture signal reduced by a correction value a(RH).

In accordance with a second aspect of the present invention, there is provided a moisture sensor comprising a capacitive moisture measuring element and a correction unit with means for carrying out the method of the first aspect of the present invention.

Advantageous configurations are set forth in the dependent claims.

BRIEF DESCRIPTION OF THE DRAWINGS

Embodiments of the invention are described in greater detail hereinafter with reference to the drawing in which.

DETAILED DESCRIPTION OF THE INVENTION

Figure 1:
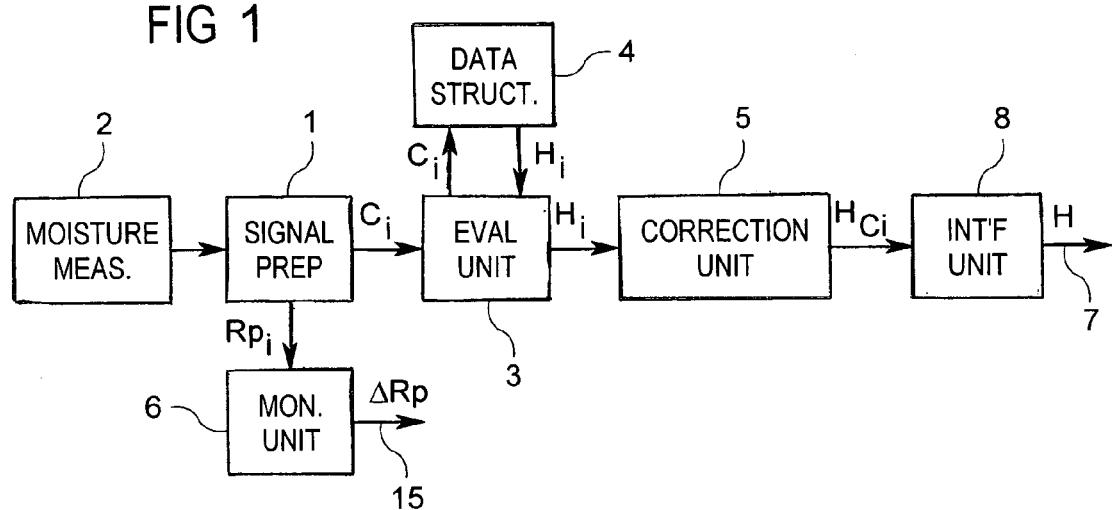
FIG. 1 shows a block circuit diagram of a moisture sensor with a capacitance moisture measuring element for determining air humidity.

A moisture sensor shown in FIG. 1 has a capacitive moisture measuring element 2 connected to a signal preparation unit 1 and an evaluation unit 3 connected on the output side of the signal preparation unit 1.

In an advantageous implementation the moisture sensor also has a data structure 4 which can be used for the evaluation unit 3. For further improving the properties involved the moisture sensor can be supplemented by a correction unit 5 connected on the output side of the evaluation unit 3 and/or a monitoring unit 6 connected to the signal preparation unit 1. A moisture signal H at an output 7 of the moisture sensor can advantageously be matched by way of an interface unit 8.

Depending on the respective requirements involved the moisture signal H in the interface unit is prepared for a standard provided at the output 7, for example in the form of a digital signal and/or in the form of an analog signal.

Certain electrical properties such as a capacitance or an ohmic resistance of the capacitive moisture measuring element 2 can be altered by the humidity of the ambient air surrounding the moisture measuring element 2, in such a way that they can be detected by the signal preparation unit 1.

When the demands made on the level of measuring accuracy are high the moisture measuring element 2 cannot be modelled as an ideal capacitor—that is to say as pure capacitance. It has been found however that, in a frequency range between zero and about 50 kHz, the moisture measuring element 2 can be modelled to a good approximation by a parallel circuit of a variable capacitance C and a variable ohmic resistance Rp. The values of the capacitance C and the resistance Rp are dependent not only on the moisture level but also on temperature and in addition generally involve scatter within a production series.

A current capacitance value Ci of the moisture measuring element 2 is ascertained by the signal preparation unit 1 and made available to the evaluation unit 3 for calculating the air humidity value Hi which prevails at the moisture measuring element 2. The air humidity value Hi is advantageously calculated by means of the data structure 4 for the current capacitance value Ci. The data structure 4 is for example a table or a mathematical relationship between the capacitance C and air humidity, wherein if required still further parameters—for example the air temperature—are also incorporated. The moisture sensor is generally to be designed in such a way that the moisture signal which it generates is a measurement in respect of relative air humidity RH. For example a range of values of between 0%rh and 100%rh is associated with the relative air humidity.

Figure 2:
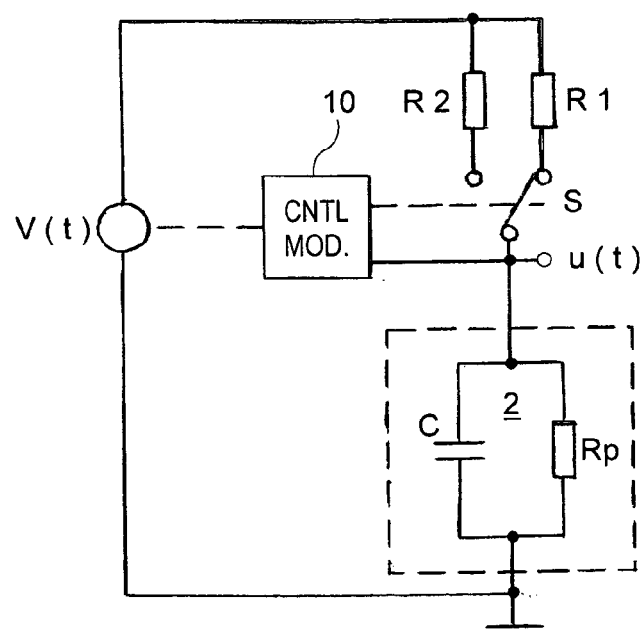
FIG. 2 shows a general circuit for measurement determination on the part of the capacitive moisture measuring element.

FIG. 2 shows the moisture measuring element 2 in broken line, being modelled by the parallel circuit of the capacitance C and the ohmic resistance Rp. In order to ascertain the current capacitance value Ci or a current resistance value Rpi of the model the moisture measuring element 2, in accordance with the invention, is charged and/or discharged by a voltage source V(t) and a change-over switch S in a first measuring run by way of a first measuring resistor R1 and also charged and/or discharged in a second measuring run by way of a second measuring resistor R2.

In an advantageous implementation of the signal preparation unit 1 the voltage source V(t) and the change-over switch S are controlled by a control module 10. The control module 10 is embodied by way of example with a suitably programmed microcomputer or microprocessor.

The values of the two measuring resistors R1 and R2 are different and are advantageously to be selected to be smaller than the smallest expected value of the resistance Rp. In order to ascertain the current capacitance value Ci and the current resistance Rpi the configurations of the voltage u(t) across the moisture measuring element 2 are evaluated for the two measuring runs, for example by the control module 10. Either two different time constants T1 and T2 or two different period durations can advantageously be calculated from an evaluation of the two measuring runs, depending respectively on whether the moisture measuring element 2 is only charged or discharged during a measuring run, or whether it is charged and discharged in each measuring run.

By means of the two time constants T1 and T2 or the two period durations it is possible to calculate the current capacitance value Ci and the current resistance value Rpi for advantageous modelling of the moisture measuring element 2.

Periodic discharging of the moisture measuring element 2 is described by way of example hereinafter, in accordance with the diagrammatic circuit shown in FIG. 2. With this description of the measuring procedure selected, it is possible to understand conversion to an equivalent measuring run with periodic charging or also with periodic charging and discharging, without major complication.

Figure 3:
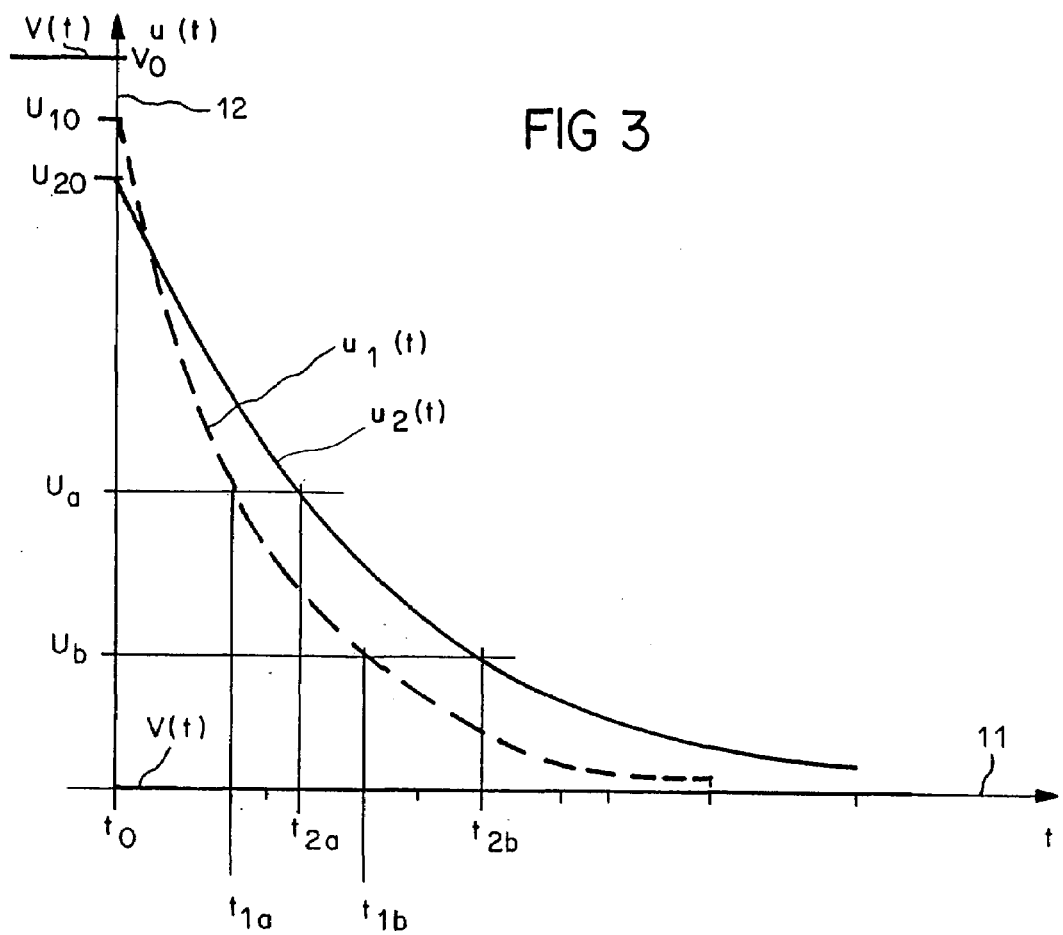
FIG. 3 shows a graph with the voltage configurations in principle at the capacitive moisture measuring element.

In FIG. 3, in relation to the circuit shown in FIG. 2, the running time t is entered in a co-ordinate system on the abscissa 11 and the voltage level is entered on the ordinate 12.

Prior to the first measuring run—at t<t0 in FIG. 3—the voltage source V(t) supplies the value V0 and the moisture measuring element 2 is charged to a value U10 in accordance with the ratio of the voltage divider formed by the first measuring resistor R1 and the ohmic resistance Rp.

From a time t0 the voltage source V(t) acts as a short-circuit so that the capacitance C of the moisture measuring element 2 is discharged by way of the resistors R1 and Rp connected in parallel with respect to the capacitance C. Discharge affords a voltage configuration u1(t) at the moisture measuring element 2.

With the e-function exp() the following applies for the voltage u1(t):

$$u1(t)=V0 \cdot (Rp/(R1+Rp)) \cdot \exp(-t/T1)$$

and the following applies for the first time constant T1:

$$T1=C/(1/R1+1/Rp) \qquad \text{(equation 1)}$$

The first time constant T1 can be calculated if two points of the configuration u1(t) are measured in the first measuring run. A first point occurs at a first voltage threshold Ua and a second point at a second voltage threshold Ub.

With U10=V0·(Rp/(R1+Rp)) the following applies for the first voltage threshold Ua:

$$Ua=U10 \cdot \exp(-t1a/T1)$$

while the following applies for the second voltage threshold Ub:

$$Ub=U10 \cdot \exp(-t1b/T1).$$

The following follows from the two equations for the voltage thresholds Ua and Ub:

$$Ua/Ub=\exp(-t1a/T1)/\exp(-t1b/T1).$$

By logarithming with the base e:

$$\ln(Ua/Ub)=(t1b/T1)-(t1a/T1).$$

And finally for the first time constant T1:

$$T1=(t1b-t1a)/\ln(Ua/Ub) \qquad \text{(equation 2)}$$

Also prior to the second measuring run—at t<t0 in FIG. 3—the voltage source V(t) delivers the value V0 and the moisture measuring element 2 is charged to a value U20 in accordance with the ratio of the voltage divider formed by the second measuring resistor R2 and the ohmic resistance Rp.

From a time t0 the voltage source V(t) acts as a short-circuit so that the capacitance C of the moisture measuring element 2 is discharged by way of the resistors R2 and Rp connected in parallel with respect to the capacitance C. Discharge gives a voltage configuration u2(t) at the moisture measuring element 2.

With the e-function exp(), the following applies for the voltage U2(t):

$$u2(t)=V0 \cdot (Rp/(R2+Rp))\exp(-t/T2)$$

while the following applies for the second time constant T2:

$$T2=C(1/R2+1/Rp) \qquad \text{(equation 3)}$$

Similarly to calculation of the first time constant T1 the second time constant T2 can be calculated if two points in respect of the configuration u2(t) are also measured in the second measuring run. A first point is at a first voltage threshold Ua and a second point at a second voltage threshold Ub.

With a time t2a for the first point in the course of the discharge u2(t) and a time t2b for the second point, the following applies in respect of the second time constant T2:

$$T2=(t2b-t2a)/\ln(Ua/Ub) \quad \text{(equation 4)}$$

With the time constants T1 and T2 ascertained in the two measuring runs it is possible to calculate the capacitance C and the ohmic resistance Rp of the moisture measuring element 2 as follows:

If equation 1 and equation 4 are resolved in accordance with 1/Rp and equated, the following applies in respect of the capacitance C of the moisture measuring element 2:

$$C=T1\cdot T2\cdot(R2-R1)/(R1\cdot R2\cdot(T2-T1)) \quad \text{(equation 5)}$$

If equation 1 and equation 4 are resolved in accordance with C and equated, the following applies in respect of the ohmic resistance Rp of the moisture measuring element 2:

$$Rp=R1\cdot R2\cdot(T2-T1)/(T1\cdot R2\cdot T2\cdot R1) \quad \text{(equation 6)}$$

The two voltage thresholds Ua and Ub are advantageously to be so selected that the two time differences t1b−t1a and t2b−t2a which are required in equation 2 and equation 4 respectively can be sufficiently accurately ascertained in terms of measurement procedure. The thresholds Ua and Ub are advantageously so selected that the times t1a, t1b, t2a and t2b of measurement occur rather in the steep region of the discharge u1(t) and u2(t), but are not too close together in terms of time. A good degree of accuracy is afforded if the first voltage threshold Ua is at 50% of the maximum voltage of the source V(t) and the second voltage threshold Ub is at 25% of the maximum voltage of the source V(t).

Figure 4:
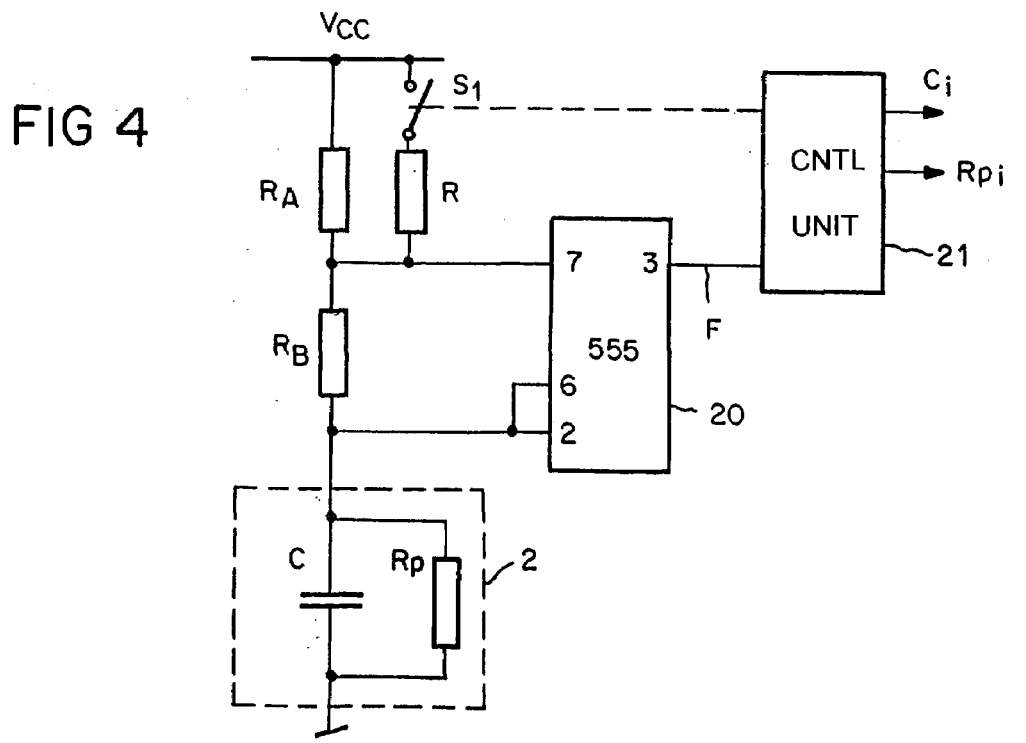
FIG. 4 shows a further circuit for measurement determination on the part of the capacitive moisture measuring element.

The current capacitance value Ci and the current resistance value Rpi of the moisture measuring element 2 can advantageously also be ascertained by means of a universal timer unit. FIG. 4 shows the circuitry in principle by means of the example of a timer unit 20 which is generally known as type 555 and is offered by a number of manufacturers and which is also offered inter alia under type designations LM1455, MC1455 or MC1555.

The timer unit 20 is connected as a multivibrator by way of the unit terminals 2 - 'trigger' -, 6 - 'threshold' - and 7 - 'discharge' -, wherein the period duration of an output signal V at the unit terminal 3 'output' of the timer unit 20 is dependent on the moisture measuring element 2 and the resistors RA, RB and R.

The resistor R can be connected in parallel with the resistor RA by way of a switch S1 actuable by a control unit 21.

In an advantageous variant of the invention the moisture measuring element 2 is charged in a first measuring run with the switch S1 in the open condition by way of the resistors RA and RB and discharged by way of the resistor RB, in that respect a first period duration of the signal F can be detected by the control unit 21.

In a second measuring run the moisture measuring element 2, with the switch S1 closed, is charged by way of the resistor RB and the parallel circuit of the resistors RA and R and discharged by way of the resistor RB, in that case a second period duration of the signal F can be detected by the control unit 21.

In this embodiment also therefore the moisture measuring element 2 is charged by the two measuring runs by way of two different resistance values so that two period durations of different lengths can be detected by the control unit 21.

Current values Ci and Rpi for the capacitance C and the ohmic resistance Rp of the moisture measuring element 2 are calculated by means of the two period durations. The control unit 21 is advantageously implemented by a microcomputer which also calculates the current values Ci and Rpi.

In an advantageous alternative configuration of the moisture sensor a change in the ohmic resistance Rp is detected by the monitoring unit 6 over a relatively long period of time, that is to say over several months or years. A greater deviation ΔRp in the value of the ohmic resistance Rp can point to an error or advanced ageing of the moisture measuring element 2. For error diagnosis, by way of example a signal corresponding to the deviation ΔRp is outputted at a further output 15 of the moisture sensor 2 (FIG. 1).

Figure 5:
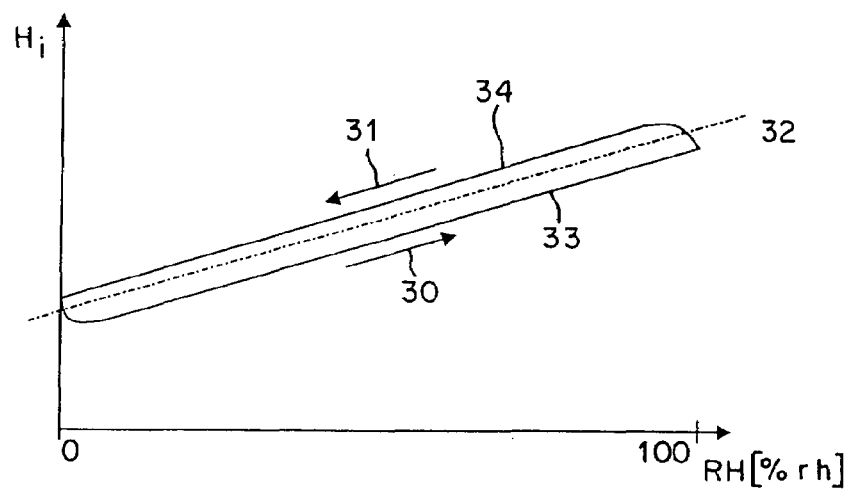
FIG. 5 shows a typical configuration of a moisture signal in a cycle having a humidification phase and a dehumidification phase.

It was possible to demonstrate that, if the moisture measuring element 2 is subjected to a cycle consisting of a humidification phase 30 and a dehumidification phase 31, the humidity value Hi measured by the moisture measuring element 2 typically follows a hysteresis 32 shown in FIG. 5. In the humidification phase 30 the humidity value Hi measured at a certain relative air humidity RH follows a lower flank 33 of the hysteresis 32 while in the dehumidification phase 31 the humidity value Hi measured at a certain relative air humidity RH follows an upper flank 34. The hysteresis 32 therefore basically acts as an error in such a way that an excessively high humidity value Hi is measured in the dehumidification phase 31 and an excessively low humidity value Hi is measured in the humidification phase 30.

Depending on the type of moisture measuring element 2 being investigated, an error caused by the hysteresis 32 is in the range of between 0.5% and 3%.

Figure 6:
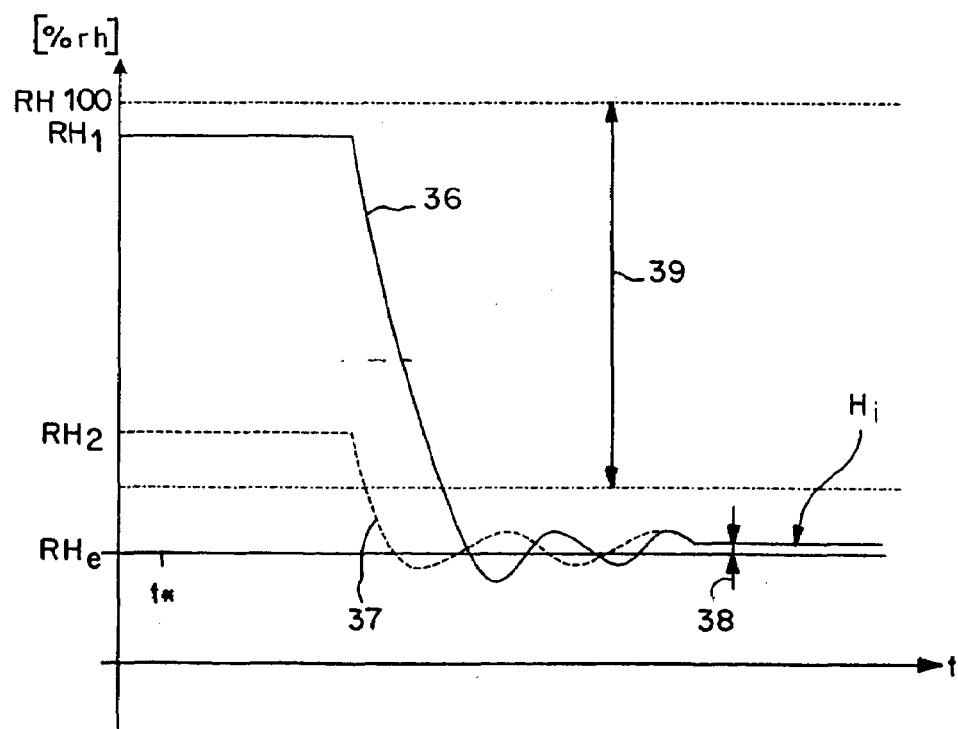
FIG. 6 shows a typical configuration of the moisture signal in response to an abrupt change in humidity.

It was also possible to show that, after abrupt changes in the relative moisture level RH in one direction (FIG. 6), the moisture measuring element 2 measures the same humidity value Hi, specifically irrespective flow of how great the abrupt change in relative moisture level RH is. That behaviour applies both in respect of abrupt dehumidification and also in respect of abrupt humidification. FIG. 6 shows by way of example a first jump response 36 and a second jump response 37, wherein the first jump response 36 occurs in response to a relative large jump from a first starting value RH1 to an end value RHe and the second jump response 37 is in response to a relatively small jump from a second starting value RH2 to an end value RHe.

Therefore after a certain time a signal from the moisture measuring element 2 also settles down to the same humidity value Hi if the change in relative moisture RH changes abruptly to the end value RHe in the same direction. Such jumps in relative moisture RH can occur for example when switching a regulating device on or off. In a regulation application of that nature, it is to be borne in mind that an error 38 caused by the hysteresis 32 (FIG. 5) can be corrected only in the steady-state condition. So that it is possible to establish in the regulating application whether the reference value has abruptly changed, it is possible for example to check whether the humidity value Hi was in a given band 39 at a certain time t* in the past, wherein the band is to be matched to the transient synchronising behaviour of the regulating application.

In order to increase the level of measuring accuracy which can be achieved a corrected moisture signal Hci is calculated for a current moisture signal Hi which is ascertained from electrical properties of the moisture measuring element 2, in which respect in a measuring phase with a rising level of relative air humidity RH the corrected moisture signal Hci is the current moisture signal Hi increased by a correction value a(RH) and wherein in a measuring phase with a falling level of relative air humidity RH the corrected moisture signal Hci is the current moisture signal Hi reduced by a correction value a(RH).

The level of measuring accuracy of the moisture sensor can be increased by a correction unit 5 in which a corrected moisture value Hci is calculated for a moisture value Hi ascertained for the moisture measuring element 2, wherein in a measuring phase with a rising relative air humidity RH the corrected moisture value Hci is the current moisture value Hi increased by a correction value a(RH) and wherein in a measuring phase with a falling relative air humidity RH the corrected moisture value Hci is the current moisture value Hi reduced by a correction value a(RH). The correction unit 5 of the moisture sensor is advantageously connected between the evaluation unit 3 and the interface unit 8.

The correction value a(RH) which is taken into consideration in the correction unit 5 is basically dependent on the relative humidity RH and is stored for example in the form of a mathematical formula or table in the correction unit 5. When the demands involved are slight or when the hysteresis 32 (FIG. 5) is of a desirable form, the required degree of measuring accuracy can possibly already be achieved if the correction value a(RH) is taken into account independently of the current relative moisture RH as a constant.

I claim:

1. A method of determining air humidity with a capacitive moisture measuring element, comprising:
    determining a current moisture signal from properties of the capacitive moisture measuring element, and
    determining a corrected moisture signal from the current moisture signal, wherein in a measuring phase with rising relative air humidity RH the corrected moisture signal is the current moisture signal increased by a correction value a(RH) and wherein in a measuring phase with falling relative air humidity RH the corrected moisture signal is the current moisture signal reduced by a correction value a(RH).

2. A method as set forth in claim 1, wherein the correction value a(RH) is constant.

3. A method as set forth in claim 1, wherein the correction value a(RH) is used from a stored table or is calculated as a mathematical function.

4. A method as set forth in claim 1, wherein charging and/or discharging the capacitive moisture measuring element by way of a first measuring resistor provides for determining a first time constant or a first period duration of the charging and/or discharging operation, and charging and/or discharging the capacitive moisture measuring element by way of a second measuring resistor, whose value is different from the value of the first measuring resistor, provides for determining a second time constant or a second period duration of the charging and/or discharging operation.

5. A method as set forth in claim 4, wherein the capacitance of the capacitive moisture measuring element is calculated from the two time constants or the two period durations, and the capacitive moisture measuring element for the calculation operation is modeled by a parallel circuit of an ideal capacitor and an ohmic resistance.

6. A method as set forth in claim 4, wherein the ohmic resistance value of the capacitive moisture measuring element is calculated from the two time constants or the two period durations, and the moisture measuring element for the calculation operation is modeled by a parallel circuit of an ideal capacitor and an ohmic resistance.

7. A method as set forth in claim 1, wherein the current moisture signal is determining with the capacitance of the capacitive moisture measuring element.

8. A moisture sensor, comprising:
    a capacitive moisture measuring element;
    a processing circuit configured to determine a current moisture signal from electrical properties of the capacitive moisture measuring element, and determine a corrected moisture signal from the current moisture signal, wherein in a measuring phase with rising relative air humidity RH the corrected moisture signal is the current moisture increased by a correction value a(RH) and wherein in a measuring phase with falling relative air humidity RH the corrected moisture signal reduced by a correction value a(RH).

9. A moisture sensor as set forth in claim 8, further comprising a monitoring unit by which a certain deviation in an ohmic resistance value of the capacitive moisture measuring element over a relatively long period of time can be detected and signalled.

10. A moisture sensor as set forth in claim 8, wherein the processing circuit includes a measurement determination unit configured to generate the current moisture signal and a correction unit configured to determine the corrected moisture signal.

11. A moisture sensor as set forth in claim 10, wherein the measurement determination unit includes a timer unit and a control unit, the timer unit configured as a multivibrator.

12. A moisture sensor as set forth in claim 10, wherein the measurement determination unit is further configured to:
    charge and/or discharge the capacitive moisture measuring element by way of a first measuring resistor to provide for determining a first time constant or a first period duration of the charging and/or discharging, and charge and/or discharge the capacitive moisture measuring element by way of a second measuring resistor, whose value is different from the value of the first measuring resistor, to provide for determining a second time constant or a second period duration of the charging and/or discharging.

13. A method of determining air humidity with a capacitive moisture measuring element, comprising:
    determining a current moisture signal from electrical properties of the moisture measuring element;
    adjusting the current moisture signal in a first direction to generate a corrected current moisture signal if a rising relative air humidity is detected; and
    adjusting the current moisture signal in a second direction to generate the corrected current moisture signal if a falling relative air humidity is detected, the second direction opposite of the first direction.

14. A method as set forth in claim 13, wherein increasing the current moisture signal includes increasing the current moisture signal by a constant correction value.

15. A method as set forth in claim 13, wherein increasing the current moisture signal includes increasing the current moisture value by a correction value obtained from a stored table.

16. A method as set forth in claim 13, wherein the current moisture signal includes increasing the current moisture value by a correction value calculated from a mathematical function.

17. A method as set forth in claim 13, wherein determining the current moisture signal further comprises:

charging and/or discharging the moisture measuring element by way of a first measuring resistor to provide for determining a first time constant or a first period duration of the charging and/or discharging operation, and charging and/or discharging the moisture measuring element by way of a second measuring resistor, whose value is different from the value of the first measuring resistor, to provide for determining a second time constant or a second period duration of the charging and/or discharging operation.

18. A method as set forth in claim 17, wherein the capacitance of the moisture measuring element is calculated from the two time constants or the two period durations, and the moisture measuring element for the calculation operation is modeled by a parallel circuit of an ideal capacitor and an ohmic resistance.

* * * * *